United States Patent [19]

Whistler

[11] 4,181,795
[45] Jan. 1, 1980

[54] DAUNOSAMINE SYNTHESIS

[75] Inventor: Roy L. Whistler, West Lafayette, Ind.

[73] Assignee: Purdue Research Foundation, West Lafayette, Ind.

[21] Appl. No.: 908,240

[22] Filed: May 22, 1978

[51] Int. Cl.$^2$ .................... C07H 15/00; C07H 17/00
[52] U.S. Cl. ........................................ 536/4; 536/18; 536/17 A; 536/17 R
[58] Field of Search ................. 536/4, 1, 17 A, 18

[56] References Cited

U.S. PATENT DOCUMENTS

| | | | |
|---|---|---|---|
| 4,020,270 | 4/1977 | Arcamone et al. | 536/17 A |
| 4,024,333 | 5/1977 | Horton et al. | 536/18 |
| 4,025,623 | 5/1977 | Arcamone et al. | 536/17 A |
| 4,039,663 | 8/1977 | Arcamone et al. | 536/17 A |

OTHER PUBLICATIONS

Horton et al., Carbohydrate Research, 44 (1975) 227–240.
Chem. Abstract, vol. 84 (1976) 165141u.
Marsh et al., Chem. Comm., 1967, p. 973.
Tronchet, J. et al., Carbohydrate Research, vol. 42, (1975) 347–351.

*Primary Examiner*—Johnnie R. Brown
*Assistant Examiner*—Blondel Hazel
*Attorney, Agent, or Firm*—Finnegan, Henderson, Farabow & Garrett

[57] ABSTRACT

A process for synthesizing daunosamine and related compounds is disclosed. Intermediates useful for synthesizing daunosamine, and processes for preparing such intermediates, are also disclosed.

21 Claims, No Drawings

DAUNOSAMINE SYNTHESIS

FIELD OF INVENTION

The present invention pertains to a technique for synthesizing daunosamine and related compounds which can be converted into daunosamine. The present invention also pertains to intermediates useful in the synthesis of daunosamine and related compounds.

BACKGROUND OF THE INVENTION

Doxorubicin is a known anthracycline antibiotic described, e.g., in U.S. Pat. No. 3,590,028. Doxorubicin, and the closely related compound daunomycin, are antineoplastic agents of established clinical utility. Doxorubicin hydrochloride, available from Adria Laboratories, Inc. under the trade name Adriamycin, has been approved by the Food and Drug Administration for use in clinical research, and is one of the most powerful anti-cancer drugs available against numerous forms of cancer.

At present, doxorubicin is produced commercially from a soil fungus by a fermentation process. A suitable fermentation technique for preparing doxorubicin is described in U.S. Pat. No. 3,590,028. Such techniques are inherently expensive and limit the types of molecules that can be produced. Because of the inherent disadvantages of presently available commercial techniques for producing doxorubicin and such related compounds as daunomycin, substantial effort has been devoted to developing processes for producing such compounds by chemical synthesis.

Doxorubicin consists of an aglycone, adriamycinone, and a sugar, daunosamine. Similarly, daunomycin consists of the aglycone daunomycinone, and the sugar daunosamine. Specifically, doxorubicin and daunomycin have the formula:

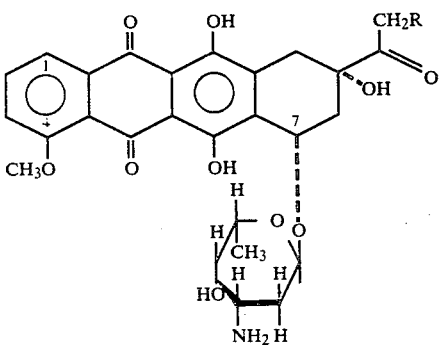

with the compound being doxorubicin when R is —OH and daunomycin when R is —H.

Techniques for synthesizing doxorubicin and daunomycin, and their aglycones, adriamycinone and daunomycinone, are known. See, e.g., Wong et al, Canadian Journal of Chemistry, Vol. 51, p. 466 (1973); Acton et al, Journal of Medicinal Chemistry, Vol. 17, No. 6, p. 659 (1974); Kende et al, Journal of American Chemical Society, Vol. 97, No. 15, p. 4425 (1975) and Vol. 98, No. 7, p. 1967 (1976); and Kende et al, U.S. Pat. No. 4,021,457. Techniques for attaching daunosamine to the aglycones are also known. See, e.g., Acton et al, supra, and Smith et al, Journal of American Chemical Society, Vol. 98, No. 7, p. 1969 (1976).

None of the known techniques for the synthesis of anthracycline antibiotics such as doxorubicin has proven to be commercially successful. Because of the demand for, and scarcity of, these compounds, a commercially practical technique for synthesizing them is greatly needed. Since the sugar daunosamine provides an important part of these compounds, and since it is known both how to synthesize the aglycones adriamycinone and daunomycinone, as well as how to attach daunosamine to the aglycones, techniques for synthesizing daunosamine, and related compounds, are highly desirable as part of a technique for the total synthesis of the anthracycline antibiotics.

While techniques for synthesizing daunosamine are known, the known techniques suffer severe shortcomings that limit their practical utility. For example, the process disclosed in Marsh et al., Chemical Communications, p. 973 (1967) uses a difficult method to obtain glycal as a starting material and involves the use of a potentially hazardous step of making an azide derivative with sodium azide. Furthermore, in the process disclosed by Marsh et al, isomers are produced that require separation by a difficult chromatographic step. The process disclosed in Horton et al, Carbohydrate Research, Vol. 44, p. 227 (1975), requires the use of a number of very expensive reagents and also results in the production of difficult to separate isomers.

The present invention provides a practical technique for synthesizing daunosamine and related compounds which can be converted to daunosamine by known techniques. Furthermore, the synthesis technique of the present invention may use, as a starting material, the readily available and inexpensive compound D-glucose. In addition, the present invention provides novel intermediates valuable in synthesizing daunosamine and related compounds.

SUMMARY OF THE INVENTION

In accordance with the present invention, the known compound 1,2:5,6-di-O-isopropylidene-3-amino-3-deoxy-α-D-allofuranose, which compound may be derived from D-glucose, is used as a starting material to produce methyl 3-substituted amino-2,3,6-trideoxy-β-L-lyxo-hexopryanoside. Techniques for converting this latter compound to daunosamine or related compounds are known in the art.

The process of the present invention for making methyl 3-substituted amino-2,3,6-trideoxy-β-L-lyxo-hexopyranoside involves:

(a) reacting 1,2:5,6-di-O-isopropylidene-3-amino-3-deoxy-α-D-allofuranose with a compound containing a blocking group whereby a blocking group is introduced on the amino group;

(b) reacting the resultant 1,2:5,6-di-O-isopropylidene-3-substituted amino-3-deoxy-α-D-allofuranose with a weak acid to produce 1,2-O-isopropylidene-3-substituted amino-3-deoxy-α-D-allofuranose;

(c) subjecting the resultant 1,2-O-isopropylidene-3-substituted amino-3-deoxy-α-D-allofuranose to benzoylation and tosylation to produce 1,2-O-isopropylidene-3-substituted amino-6-O-benzoyl-5-O-tolylsulfonyl-3-deoxy-α-D-allofuranose;

(d) removing the benzoate group and the toluene sulfonate group from the resultant 1,2-O-isopropylidene-3-substituted amino-6-O-benzoyl-5-O-tolysulfonyl-3-deoxy-α-D-allofuranose by condensing them in a lower molecular weight alcohol, under basic conditions, to produce 1,2-O-isopropylidene-3-substituted amino-5,6-anhydro-3-deoxy-β-L-talofuranose;

(e) reducing 1,2,-O-isopropylidene-3-substituted amino-5,6-anhydro-3-deoxy-β-L-talofuranose to produce 1,2,-O-isopropylidene-3-substituted amino-3,6-dideoxy-β-L-talofuranose;

(f) reacting the resultant 1,2-O-isopropylidene-3-substituted amino-3,6-dideoxy-β-L-talofuranose with a strong acid and reacting the resultant product with a compound containing a blocking group, whereby a blocking group containing product is formed corresponding to the formula

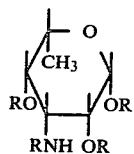

wherein R is a blocking group;

(g) halogenating, and preferably chlorinating or brominating, the resultant blocking group containing product to produce a halogenated derivative corresponding to the formula

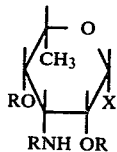

wherein R is a blocking group and X is a halogen, preferably Cl or Br, and a mixture or anomeric forms may be present;

(h) reducing the resultant halogenated derivative to form a glycal having the formula

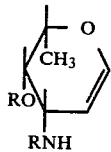

wherein R is a blocking group; and (i) subjecting said glycal to methoxymercuration and reducing the resultant product whereby methyl 3-substituted amino-2,3,6-trideoxy-βL-lyxo-hexopyranoside is formed.

The methyl 3-substituted amino-2,3,6,-trideoxy-β-L-lyxo-hexopyranoside may be converted to daunosamine hydrochloride by reacting with hydrochloric acid. Other methods for converting analogous compounds into daunosamine and other related compounds, which themselves may be useful in synthesizing adriamycin nd daunomycin, are disclosed in Marsh et al, Chemical Communications, p. 973 (1967).

The present invention also pertains to novel intermediates useful in synthesizing daunomycin. Among such compounds are those having the formula:

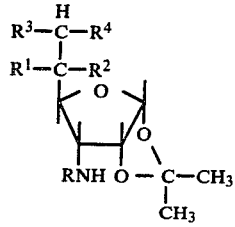

wherein
R is H,

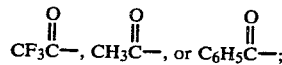

$R^1$ is H, HO—, or $CH_3C_6H_4SO_2O$—; $CH_3SO_2O$—;
$R^2$ is H, —OH, or, in combination with $R^4$, >O;
$R^3$ is H, HO-, or

and
$R^4$ is H or, in combination with $R^2$, >O; provided that one of $R^1$ or $R^2$ and one of $R^3$ or $R^4$ must in all cases, be H. Thus, for example when $R^2$ and $R^4$ combined are >O, $R^1$ and $R^3$ are H.

The present invention additionally provides valuable intermediates useful in preparing daunosamine and related compounds including those having the formula:

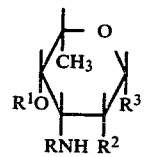

wherein
R and $R^1$ which may be the same or different, are

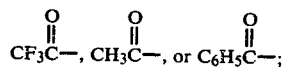

$R^2$ is

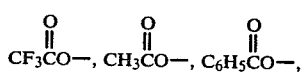

or, in combination with $R^3$, forms a double bond;
and
$R^3$ is

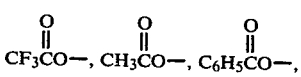

Cl, Br—, or, in combination with $R^2$, forms a double bond.

DESCRIPTION OF PREFERRED EMBODIMENTS

In the synthesis technique of the present invention D-glucose may be used as a starting material. D-glucose is a readily available and inexpensive compound having the formula:

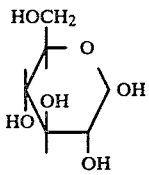
1.

It should be noted that in the above structural formula, as well as in other structural formulas appearing herein, some of the hydrogen atoms are omitted for purposes of clarity. Those skilled in the art, however, will have no trouble comprehending the formulas to include the omitted hydrogen atoms.

D-Glucose is first condensed with acetone to yield 1,2:5,6-di-O-isopropylidene-α-D-glucofuranose hving the formula:

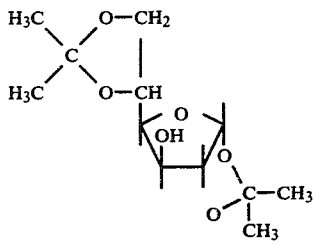
2.

Condensation is preferably effected in the presence of dehydrating and condensing agents such as zinc chloride and phosphoric acid or cupric sulfate and sulfuric acid.

The condensation product may be recovered by first removing insoluble materials by filtration, evaporating the filtrate to a heavy syrup, diluting the syrup with a solvent such as chloroform, and extracting the solution with water. The water extract may be concentrated by evaporation to give a crude compound which may be purified by crystallization from a solvent such as a chloroform-hexane mixture.

The condensation product of formula 2 may be next oxidized to 1,2,:5,6-di-O-isopropylidene-α-D-ribo-hexofuranos-3-ulose having the formula:

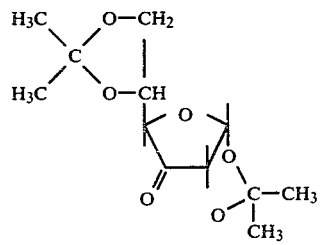
3.

Oxidation of the condensation product of formula 2 may be effected with phosphorous pentoxide in dimethyl sulfoxide, following the technique disclosed in Onodera et al., Carbohydrate Research, Vol., 6, pp. 276–285 (1968). Preferably, however, oxidation is effected with a mixture of dimethyl sulfoxide and acetic anhydride. Other oxidants such as ruthenium tetraoxide also may be used. After extraction with water and chloroform, the product may be recovered by evaporation of the chloroform solution and purified by recrystallizing from a solvent such as light petroleum.

The ketose of formula 3 may be converted to the oxime by reacting with hydroxylamine, to the thiosemicarbazone by reacting with thiosemicarbazide, or to the semicarbazone by reacting with semicarbazide, following the technique of Onodera et al. to yield 1,2:5,6-di-O-isopropylidene-α-D-ribo-hexofuranos-3-ulose oxime of the formula:

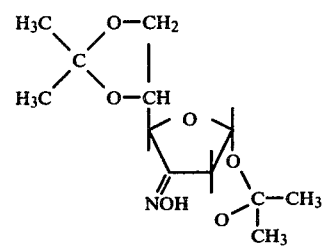
4.

or isopropylidene-α-D-ribo-hexofuranos-3-ulose thiosemicarbazone or isopropylidene-α-D-ribo-hexofuranos-3-ulose semicarbazone. Preferably, the reaction is carried out by refluxing in a solvent such as ethanol and pyridine, and the product is recovered by evaporation to a heavy syrup and crystallizing from petroleum ether.

The oxime of formula 4 (or the corresponding thiosemicarbazone or semicarbazone) is converted to an allo-amine by reducing the compound to yield 1,2:5,6-di-O-isopropylidene-3-amino-3-deoxy-α-D-allofuranose having the formula:

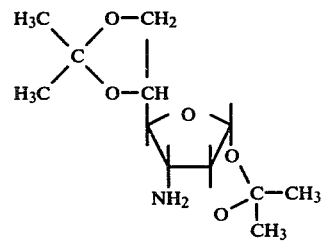
5.

Preferably, the reduction is effected with lithium aluminum hydride, but other reduction techniques, such as hydrogen catalyzed by platinum, palladium or nickel, may be used.

The allo-amine of formula 5 is next reacted with a compound which will introduce a blocking group on the amino group to produce a compound having the formula:

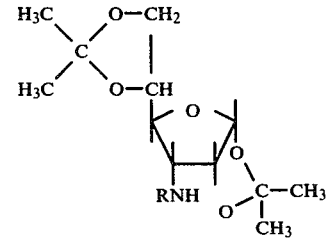
6.

where R is the blocking group.

Examples of suitable blocking groups which may be used throughout the present synthesis technique include trifluoroacetyl, acetyl, and benzoyl groups. These groups may be introduced by reacting, e.g., the allo-amine with, respectively, such compounds as trifluoroacetic anhydride, acetic anhydride, or benzoyl chloride. The preferred reactant for use with the allo-amine is trifluoroacetic anhydride, whereby 1,2:5,6-di-O-isopropylidene-3-trifluoroacetamido-3-deoxy-α-D-allofuranose is produced.

At this stage, or at any other stage where desired, the blocking group may be removed using known techniques. Such techniques include, depending on the location of the blocking group, saponification or reacting with a strong acid, e.g., hydrochloric acid.

The product obtained by reacting the allo-amine of formula 5 with the blocking group containing compound is next reacted with a weak acid, such as acetic acid, to produce 1,2-O-isopropylidene-3-substituted amino-3-deoxy-α-D-allofuranose of the formula:

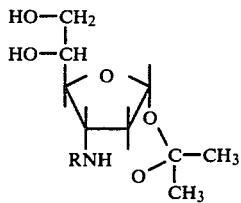
7.

where R is the blocking group. When R is the preferred trifluoroacetyl group, this compound would be 1,2-O-isopropylidene-3-trifluoroacetamido-3-deoxy-α-D-allofuranose. The product of formula 7 may be recovered by evaporating to a heavy syrup and crystallizing from a solvent such as an acetone-ether mixture.

The 1,2-O-isopropylidene-3-substituted amino-3-deoxy-α-D-allofuranose of formula 7 is next subjected to benzoylation and tosylation to produce a 1,2-O-isopropylidene-3-substituted amino-5-O-tolylsulfonyl-6-O-benzoyl-3-deoxy-α-D-allofuranose having the formula:

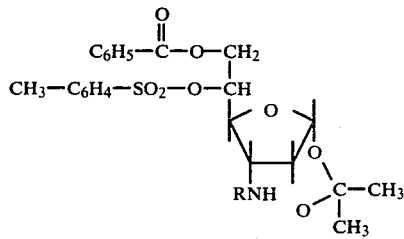
8.

where R is the blocking group, preferably a trifluoroacetyl group. When R is a trifluoroacetyl group, the compound of formula 8 is 1,2-O-isopropylidene-3-trifluoroacetamido-5-O-tolylsulfonyl-6-O-benzoyl-3-deoxy-α-D-allofuranose.

The benzoylation and tosylation or mesylation are preferably conducted sequentially whereby a solution of the compound of formula 7 is first reacted with benzoyl chloride to produce the 6-O-benzoyl derivative of the compound of formula 7, which compound is subsequently reacted with a solution of p-tolylsulfonyl chloride to produce the compound of formula 8. The resultant product may be recovered by extracting with chloroform, washing with water, drying, evaporating to a heavy syrup, and crystallizing from a solvent such as a mixture of ether and petroleum ether.

The benzoate and toluene sulfonate groups are next removed by condensing the blocking group, the benzoate group and the toluene sulfonate group, under basic conditions, with a lower molecular weight alcohol, e.g., a $C_1$ to $C_6$ alcohol, to produce 1,2-O-isopropylidene-3-substituted amino-5,6-anhydro-3-deoxy-β-L-talofuranose having the formula:

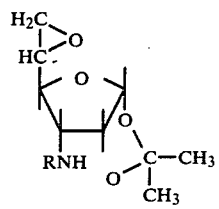
10.

Preferably the benzoate group, and the p-toluene sulfonate group are condensed with methyl alcohol in the presence of sodium methoxide. The product may be recovered by extraction with chloroform, washing with water, drying, and evaporating the solvent. Under mild reaction conditions, the blocking group, if such as an acetyl group, may remain on the nitrogen.

The anhydro-talofuranose is next reduced to produce 1,2-O-isopropylidene-3-substituted amino-3,6-dideoxy-β-L-talofuranose having the formula:

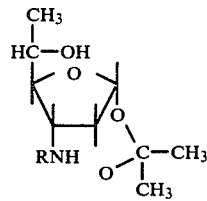
10.

Any one of a number of known reducing techniques and reagents may be employed. For example, the anhydro compound can be reduced by using a metallic catalyst, such as Raney nickel or with lithium aluminum hydride or other common reducing agents. The reducing technique should be conducted in such a way as to ensure that an alkyl group is not left on the nitrogen.

If reduction is carried out with a hydride, excess hydride can be decomposed with ethyl acetate, and the desired deoxy compound recovered by treating with a dilute sodium hydroxide solution, extracting with ethyl acetate, and evaporating to remove the solvent. The 3,6-dideoxy compound is recovered in the form of a heavy syrup.

The 3,6-dideoxy compound of formula 10 is reacted with a strong acid and, after completion of the reaction, the reaction mixture may be neutralized and a precipitate recovered by filtration. The residue remaining after evaporating the filtrate to dryness is dissolved in a solvent and reacted with a compound containing a blocking group, whereby a product is produced corresponding to the following formula:

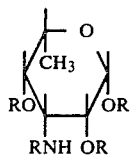

where R is a blocking group, e.g., a trifluoroacetyl, an acetyl or a benzoyl group.

The blocking group on the amino substituent may be different from the other blocking groups. Preferably, the blocking groups are acetyl groups other than the amino blocking group, which may be introduced by reacting with acetic anhydride, whereby 3-substituted amino-1,2,4-tri-O-acetyl-3,6-dideoxy-β-L-talopyranose is produced. The reaction is preferably conducted in a solvent which is a good acid acceptor, such as pyridine, a sodium hydroxide solution or quinoline.

The compound of formula 11 is next halogenated, and preferably chlorinated or brominated to produce a compound corresponding to the formula:

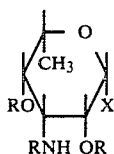

where R is a blocking group and X is halogen, preferably chlorine or bromine. The compound of formula 11 can be halogenated by any number of known techniques but, preferably, the halogenation is effected by reacting with hydrogen bromide in acetic acid. When the blocking groups are the preferred acetyl groups, 3-acetamido-2,4-di-O-acetyl-3,6-dideoxy-β-L-talopyranosyl bromide is thus produced.

The product may be recovered by adding the reaction mixture to a solvent, neutralizing the hydrogen bromide and acetic acid, washing with water, evaporating to a heavy syrup, crystallizing by adding ether, and recrystallizing the product from a chloroform-ether mixture.

The product of formula 12 is next reduced whereby an acetate halide is removed and a glycal is produced, which glycal has the formula:

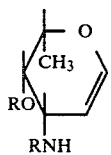

where R is the same blocking group as in formula 11. In accordance with the preferred embodiment of the present invention, this compound would be 3-acetamido-4-O-acetyl-1,2,3,6-tetradeoxy-β-L-lyxo-hex-1-enepyranose.

Preferably, the acetate halide group is removed by reducing with zinc dust in the presence of a cupric sulfate catalyst. The reaction may be carried out in a solvent such as acetic acid, and the product may be recovered by extracting with chloroform, washing, drying, evaporating to a heavy syrup, and crystallizing from a mixture of ether and petroleum ether.

The glycal of formula 13 may be converted to methyl 3-substituted amino-2,3,6-trideoxy-β-L-lyxo-hexopyranoside having the formula:

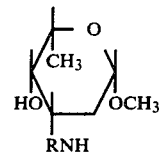

where R is a blocking group, by subjecting the glycal to methoxymercuration and reducing the resultant product. Preferably, the methoxymercuration is effected using mercuric acetate and methanol, and the reduction is effected with sodium borohydride. The preferred product of this step would be methyl-3-acetamido-2,3,6-trideoxy-β-L-lyxo-hexopyranoside.

3-Amino-2,3,6-trideoxy-β-L-lyxo-hexose (daunosamine hydrochloride) having the formula:

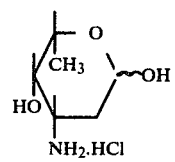

can be produced from the compound of formula 14 by hydrolyzing in hydrochloric acid. Such a technique is shown in Marsh et al., supra.

Alternatively, the compound of formula 14 can be converted to a compound having the formula

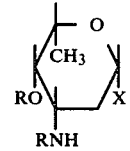

where R is a blocking group, such as an acetyl, benzoyl, or trifluoroacetyl group, and X is chlorine or bromine, by reacting the compound of formula 14 with a compound or compounds comprising a blocking group and a chlorine or bromine group. Examples of suitable reagents include acetyl bromide, hydrogen bromide and acetic acid, acetyl chloride, or acetic acid and hydrochloric acid.

Daunosamine hydrochloride, or a compound of formula 16, can be reacted with the aglycones, adriamycinone or daunomycinone, using techniques known in the art. For example, the aglycones and daunosamine hydrochloride, or a product of formula 16, can be condensed under basic conditions, as for example in the presence of sodium methoxide in methanol. When daunosamine hydrochloride is employed as a reactant, Adriamycin ® or daunomycin hydrochloride is produced, depending on aglycone employed. Where the compound of formula 16 is employed, the resultant product can be converted to doxorubicin or daunomycin after condensing by removing the blocking groups, using such known techniques as hydrolyzing in hydrochloric acid or saponifying.

The following examples further illustrate preferred embodiments of the present invention. The examples should in no way be considered limiting, but are merely illustrative of the various features of the present invention.

EXAMPLE 1

To a suspension of 100 grams of anhydrous D-glucose in one liter of anhydrous acetone is added 80 grams of anhydrous zinc chloride and 5 grams of 85% phosphoric acid. The mixture is stirred for 30 hours at room temperature and then neutralized with a 50% NaOH solution. The insoluble materials are removed by filtration and washed with acetone. The combined filtrates are evaporated under reduced pressure to heavy syrup and the residual syrup is diluted with 500 ml. of chloroform. The chloroform solution is extracted three times with water and concentrated in vacuo to give crude 1,2:5,6-di-O-isopropylidene-α-D-glucofuranose. The crude product is purified by crystallization from a chloroform and hexane mixture to give 77 grams (91% yield based on the D-glucose consumed) of a pure product having a melting point of 105°–109° C.

EXAMPLE 2

100 g. of the product of Example 1 was dissolved in a mixture of 900 ml. of dimethylsulfoxide and 300 ml. of acetic anhydride and stirred for 24 hours at 25° C. The reaction mixture was evaporated at 0.05–0.1 Torr to a heavy syrup, which was dissolved in 500 ml. of toluene and then evaporated at 0.05–0.1 Torr. Co-evaporation with toluene was repeated (about 3 times) until dimethylsulfoxide and acetic anhydride were completely removed. The yield of the syrupy residue (crude 1,2:5,6-di-O-isopropylidene-α-D-ribo-hexofuranose-3-ulose) was 100 g.

Although it is not essential, the crude product may be purified, if desired, by extracting with chloroform, evaporating the chloroform solution in vacuo, and recrystallizing from light petroleum ether (boiling point 30°–60° C.). The purified product is a white crystalline material having a melting point of 108°–112° C.

EXAMPLE 3

To a solution of the syrupy residue (100 g.) produced in accordance with Example 2, in a mixture of 700 ml. of pyridine and 300 ml. of ethanol, 100 g. of hydroxylamine hydrochloride was added. The reaction mixture was refluxed for 2 to 3 hours and then evaporated to dryness at 20–30 Torr. The residue was dissolved in 1500 ml. of chloroform (or dichloromethane) and the organic solution was washed with water and cold dilute sodium bisulfate solution. The chloroform layer was evaporated to dryness at 20–30 Torr after being dried over anhydrous magnesium sulfate. The residue thus obtained was crystallized from an ether-petroleum ether mixture (boiling point 30°–60° C.) to give 52.5 g. of 1,2:5,6-di-O-isopropylidene-α-D-ribo-hexofuranose-3-ulose oxime having a melting point of 102°–103° C. A second batch of crystalline product (24.0 g.) was recovered from the mother liquor to give a total yield of about 65% based on the product of Example 1.

EXAMPLE 4

While cooling in an ice bath, 40 g. of lithium aluminum hydride was added to a solution, in 2000 ml. of anhydrous tetrahydrofuran, of 50 g. of the oxime produced by the process of Example 3. The reaction mixture was refluxed for 3 hours under conditions such that moisture was excluded from the reaction mixture. After refluxing, 2000 ml. of ethyl acetate were added to the reaction mixture at 25° C., the resultant solution was stirred for 1 hour and poured into about 2000 ml. of crushed ice. The liquid layer was separated from the inorganic gel by filtration and the gel was washed with 2000 ml. of chloroform. The organic layer separated from the combined filtrate was washed with water. After being dried with anhydrous magnesium sulfate, the solution was evaporated to dryness at 20–30 Torr. The residue was crystallized from ether to give 29.0 g. of 1,2:5,6-di-O-isopropylidene-3-amino-3-deoxy-α-D-allofuranose (melting point 91°–92° C.).

EXAMPLE 5

While cooling in an ice bath, seven grams of the product of Example 4 was dissolved in the mixture of 100 ml. of anhydrous pyridine and 20 ml. of trifluoroacetic anhydride. The reaction mixture is evaporated under reduced pressure and the residue is crystallized from a chloroform-ether-hexane mixture to give 8.2 g. (63% yield) of 1,2:5,6-di-O-isopropylidene-3-trifluoroacetamido-3-deoxy-α-D-allofuranose (melting point 120°–121° C.).

EXAMPLE 6

A solution of 10 g. of the product of Example 5 in 150 ml. of 50% aqueous acetic acid is stirred at 25° C. for 10 hours and then evaporated under reduced pressure to a heavy syrup. The syrup is crystallized from an acetone-ether mixture to give 8 g. (89% yield) of 1,2-O-isopropylidene-3-trifluoroacetamido-3-deoxy-α-D-allofuranose.

EXAMPLE 7

To a solution of 10 g. of the compound of Example 6 in 100 ml. of pyridine, 4 ml. of benzoyl chloride in 4 ml. of chloroform is added dropwise at −15° C. The reaction mixture is stirred at 0° C. for 6 hours, poured into 200 ml. of ice and water, and the aqueous solution is extracted five times with chloroform. The combined chloroform extracts are washed, while cooling, with water, dilute hydrochloric acid, dilute sodium hydroxide solution, and finally water. After drying with anhydrous magnesium sulfate, the chloroform solution is evaporated under reduced pressure to a heavy syrup.

The syrup is dissolved in a solution of 15 g. of p-tolylsulfonyl chloride in 50 ml. of pyridine, the reaction mixture stirred for 20 hours at 40° C., and poured into 200 ml. of ice and water. The aqueous solution is extracted five times with 100 ml. of chloroform and the combined chloroform extracts are washed with water and dried over anhydrous magnesium sulfate. The chloroform solution is evaporated under reduced pressure to a heavy syrup, which is crystallized from a mixture of ether-petroleum ether (boiling point 30°–60° C.) to give 16 g. (89% yield) of 1,2-O-isopropylidene-3-trifluoroacetamido-5-O-tolylsulfonyl-6-O-benzoyl-3-deoxy-α-D-allofuranose.

EXAMPLE 8

To a solution of 10 g. of the compound of Example 7 in 70 ml. of chloroform, sodium methoxide (equivalent to 1.1 g. of sodium) in 20 ml. of anhydrous methanol is added dropwise at −15° C. The reaction mixture is stirred overnight at 0° C. and poured into 175 ml. of ice and water. The aqueous solution is extracted five times with 25 ml. of chloroform and the combined extracts are washed with water until neutral. The chloroform solution is dried over anhydrous magnesium sulfate and evaporated under reduced pressure to give 3.4 g. (97% yield) of a syrup. The syrup, which is chromatographically pure, is 1,2-O-isopropylidene-3-trifluroacetamido-5,6-anhydro-3-deoxy-$\beta$-L-talofuranose.

EXAMPLE 9

A reaction mixture consisting of 10 g. of the compound produced in accordance with Example 8 and 1 g. of palladium catalyst in 100 ml. of methanol is hydrogenated under 45 psi at 25° C. for 12 hours. The mixture is filtered and evaporated at reduced pressure, leaving 6 g. (59% yield) of a heavy syrup constituting 1,2-O-isopropylidene-3-trifluoroacetamido-3,6-dideoxy-$\beta$-L-talofuranose.

EXAMPLES 10 AND 11

A solution of 10 g. of the compound of Example 9 in 200 ml. of 0.05 N sulfuric acid is heated at 100° C. for 1 hour. The reaction mixture is then neutralized with barium carbonate, the precipitate is removed by filtration, and the filtrate evaporated in vacuo to dryness. The residue is dissolved in 300 ml. of anhydrous pyridine and 30 ml. of acetic anhydride, and the reaction is continued overnight at room temperature.

The residue obtained from the reaction mixture by evaporation in vacuo, which consists of 3-trifluoroacetamido-1,2,4-tri-O-acetyl-3,6-dideoxy-$\beta$-L-talopyranose, is dissolved in 20 ml. of a 30% hydrogen bromide-acetic acid solution. After being kept for 2 hours at room temperature, 200 ml. of chloroform is added to the reaction mixture and the chloroform solution is washed with ice and water, a cold saturated sodium hydrogen carbonate solution, and water. The solution is dried over anhydrous magnesium sulfate and evaporated under reduced pressure to heavy syrup. The syrup is crystallized by adding ether, and recrystallization from a mixture of chloroform-ether gives 16 g. (92% yield) of 3-trifluoroacetamido-2,4-di-O-acetyl-3,6-dideoxy-$\beta$-L-talopyranosyl bromide.

EXAMPLE 12

To a mixture of 18 g. of zinc dust and 1.8 g. of cupric sulfate in 60 ml. of 50% aqueous acetic acid containing 25 g. of sodium acetate, 10 g. of the product of Examples 10 and 11 in 10 ml. of acetic acid is added dropwise at −10° C. The reaction is continued for 4 hours at −10° C., after which the zinc dust and copper are removed by filtration, 50 g. of ice is added to the filtrate, and the filtrate is extracted three times with chloroform. The combined extracts are washed with water, a cold saturated sodium hydrogen carbonate solution, and water. After the chloroform solution is dried over anhydrous magnesium sulfate, it is evaporated in vacuo to a heavy syrup. The syrupy residue is crystallized from a mixture of ether-petroleum ether to give 4.7 g. (77% yield) of 3-trifluoroacetamido-4-O-acetyl-1,2,3,6-tetradeoxy-L-lyxo-hex-1-enepyranose.

EXAMPLE 13

To a solution of 12.4 g. of mercuric acetate in 150 ml. of methanol, 10 g. of the product of Example 12 in 40 ml. of methanol is added and the reaction mixture is stirred for 3 hours at room temperature. After the addition, with cooling, of 200 ml. of 1 N sodium hydroxide solution, 0.54 g. of sodium borohydride in 10 ml. of 1 N sodium hydroxide solution is added dropwise. The reaction mixture is kept for 5 hours at room temperature and then neutralized with acetic acid. The aqueous solution obtained by evaporating the methanol under reduced pressure is extracted five times with 100 ml. of chloroform and the combined chloroform extracts are washed with water and dried over anhydrous magnesium sulfate. The chloroform solution is evaporated under reduced pressure to a heavy syrup, and the residue is crystallized from an acetone-petroleum ether mixture to give 7 g. (96% yield) of methyl-3-trifluoroacetamido-2,3,6-trideoxy-$\beta$-L-lyxo-hexopyranoside.

EXAMPLE 14

A solution of 10 g. of the product of Example 13 in 200 ml. of 1 N hydrochloric acid solution is heated for 4 hours at 100° C., and then evaporated in vacuo to a heavy syrup. The heavy syrup is readily crystallized on addition of acetone to give 8.4 g. (71% yield) of 3-amino-2,3,6-trideoxy-$\beta$-L-lyxo-hexose hydrochloride (daunosamine hydrochloride).

Although the present invention has been described in connection with preferred embodiments, it is understood that modifications and variations may be resorted to without departing from the spirit and scope of the invention. Such modifications are considered to be within the purview and scope of the invention and the appended claims.

What is claimed is:

1. A process for making methyl 3-substituted amino-2,3,6,-trideoxy-$\beta$-L-lyxo-hexopyranoside comprising:
   (a) reacting 1,2:5,6-di-O-isopropylidene-3-amino-3-deoxy-$\alpha$-D-allofuranose with a compound containing a blocking group whereby a blocking group is introduced on the amino group;
   (b) reacting the resultant 1,2:5,6-di-O-isopropylidene-3-substituted amino-3-deoxy-$\alpha$-D-allofuranose with a weak acid to produce 1,2-O-isopropylidene-3-substituted amino-3-deoxy-$\alpha$-D-allofuranose;
   (c) subjecting the resultant 1,2-O-isopropylidene-3-substituted amino-3-deoxy-$\alpha$-D-allofuranose to benzoylation and tosylation to produce 1,2-O-isopropylidene-3-substituted amino-6-O-benzoyl-5-O-tolylsulfonyl-3-deoxy-$\alpha$-D-allofuranose;
   (d) removing the benzoate group, and the toluene sulfonate group from the resultant 1,2-O-isopropylidene-3-substituted amino-6-O-benzoyl-5-O-tolylsulfonyl-3-deoxy-$\alpha$-D-allofuranose by condensing them in a low molecular weight alcohol, under basic conditions, to produce 1,2-O-isopropylidene-3-substituted amino-5,6-anhydro-3-deoxy-$\beta$-L-talofuranose;
   (e) reducing 1,2,-O-isopropylidene-3-substituted amino-5,6-anhydro-3-dideoxy-$\beta$-L-talofuranose to produce 1,2,-O-isopropylidene-3-substituted amino-3,6-deoxy-$\beta$-L-talofuranose;
   (f) reacting the resultant 1,2-O-isopropylidene-3-substituted amino-3,6-dideoxy-$\beta$-L-talofuranose with a strong acid and reacting the resultant product with a compound containing a blocking group, whereby a blocking group containing product is formed corresponding to the formula

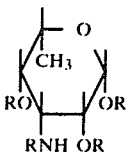

wherein R is a blocking group:
(g) halogenating the resultant blocking group containing product to produce a halogenated derivative corresponding to the formula

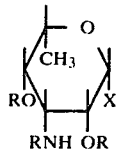

wherein R is a blocking group and X is halogen;
(h) reducing the resultant chlorinated or brominated derivative to form a glycal having the formula

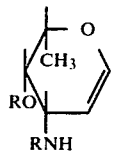

wherein R is said blocking group; and
(i) subjecting said glycal to methoxymercuration and reducing the resultant product whereby methyl 3-substituted amino-2,3,6,-trideoxy-β-L-lyxo-hexopyranoside is formed.

2. The process of claim 1 where the 1,2:5,6-di-O-isopropylidene-3-amino-3-deoxy-α-D-allofuranose is prepared by reacting D-glucose with acetone to produce 1,2:5,6-di-O-isopropylidene-α-D-glucofuranose, oxidizing the glucofuranose to produce 1,2:5,6-di-O-isopropylidene-α-D-ribo-hexofuranose-3-ulose, subjecting the hexofuranose to oximization to produce 1,2:5,6-di-O-isopropylidene-α-D-ribo-hexofuranose-3-ulose oxime, and reducing the oxime to produce said 1,2:5,6-di-O-isopropylidene-3-amino-3-deoxy-α-D-allofuranose.

3. The process of claim 1 wherein said methyl-3-substituted amino-2,3,6-trideoxy-β-L-lyxo-hexopyranoside is converted to daunosamine hydrochloride by reacting said hexopyranoside with hydrochloric acid.

4. The process of claim 1 wherein said methyl 3-substituted amino-2,3,6-trideoxy-β-L-lyxo-hexopyranoside is converted to a compound having the formula:

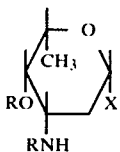

by reacting said hexopyranoside with a reagent selected from the group consisting of (1) RX or (2) HX and ROH, wherein R is

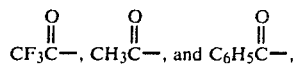

and X is Cl or Br.

5. A process for producing 1,2:5,6-di-O-isopropylidene-3-trifluoroacetamido-3-deoxy-α-D-allofuranose comprising reacting 1,2:5,6-di-O-isopropylidene-3-amino-3-deoxy-α-D-allofuranose with trifluoroacetic anhydride whereby said 1,2:5,6-di-O-isopropylidene-3-trifluoroacetamido-3-deoxy-α-D-allofuranose is formed.

6. A process for producing 1,2-O-isopropylidene-3-trifluoroacetamido-3-deoxy-α-D-allofuranose comprising reacting 1,2:5,6-di-O-isopropylidene-3-trifluoroacetamido-3-deoxy-α-D-allofuranose with acetic acid whereby said 1,2-O-isopropylidene-3-trifluoroacetamido-3-deoxy-α-D-allofuranose is formed.

7. A process for producing 1,2-O-isopropylidene-3-trifluoroacetamido-6-O-benzoyl-5-O-tolylsulfonyl-3-deoxy-α-D-allofuranose which comprises reacting 1,2-O-isopropylidene-3-trifluoroacetamido-3-deoxy-α-D-allofuranose with benzoyl chloride and tolylsulfonyl chloride whereby 1,2-O-isopropylidene-3-trifluoroacetamido-6-O-benzoyl-5-O-tolylsulfonyl-3-deoxy-α-D-allofuranose is formed.

8. A process for producing 1,2-O-isopropylidene-3-trifluoroacetamido-5,6-anhydro-3-deoxy-β-L-talofuranose which comprises reacting 1,2-O-isopropylidene-3-trifluoroacetamido-6-O-benzoyl-5-O-tolylsulfonyl-3-deoxy-α-D-allofuranose with a solution of sodium methoxide in methyl alcohol whereby 1,2-O-isopropylidene-3-trifluoroacetamido-5,6-anhydro-3-deoxy-β-L-talofuranose is produced.

9. A process for producing 1,2-O-isopropylidene-3-trifluoroacetamido-3,6-dideoxy-β-L-talofuranose comprising reducing 1,2-O-isopropylidene-3-trifluoroacetamido-5,6-anhydro-3-deoxy-β-L-talofuranose with a metallic catalyst whereby said 1,2-O-isopropylidene-3-trifluoroacetamido-3,6-dideoxy-β-L-talofuranose is produced.

10. A process for producing 3-trifluoroacetamido-1,2,4-tri-O-acetyl-3,6-dideoxy-β-L-talopyranose comprising reacting 1,2-O-isopropylidene-3-trifluoroacetamido-3,6-dideoxy-β-L-talofuranose with sulfuric acid and acetic anhydride, where said 3-trifluoroacetamido-1,2,4-tri-O-acetyl-3,6-dideoxy-β-L-talopyranose is produced.

11. A process for producing 3-trifluoroacetamido-2,4-di-O-acetyl-3,6-dideoxy-β-L-talopyranosyl bromide comprising reacting 3-trifluoroacetamido-1,2,4-tri-O-acetyl-3,6-dideoxy-β-L-talopyranose with hydrogen bromide whereby said 3-trifluoroacetamido-2,4-di-O-acetyl-3,6-dideoxy-β-L-talopyranosyl bromide is formed.

12. A process for producing 3-trifluoroacetamido-4-O-acetyl-1,2,3,6-tetradeoxy-L-lyxo-hex-1-enepyranose comprising reducing 3-trifluoroacetamido-2,4-di-O-acetyl-3,6-dideoxy-β-L-talopyranosyl bromide whereby said 3-trifluoroacetamido-4-O-acetyl-1,2,3,6-tetradeoxy-L-lyxo-hex-1-enepyranose is formed.

13. A process for making methyl-3-trifluoroacetamido-2,3,6-trideoxy-β-L-lyxo-hexopyranoside comprising reacting 3-trifluoroacetamido-4-O-acetyl-1,2,3,6-tetradeoxy-L-lyxo-hex-1-enepyranose with mercuric acetate and reducing the resultant product whereby methyl-3-trifluoroacetamido-2,3,6-trideoxy-β-L-lyxo-hexopyranoside is formed.

14. A compound having the formula

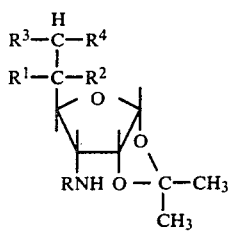

wherein
R is H,

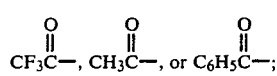

$R^1$ is H, HO-, $CH_3C_6H_4SO_2O-$; or $CH_3SO_2O-$;
$R^2$ is H, —OH, or, in combination with $R^4$, >O;
$R^3$ is H, HO—, or

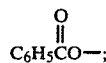

and
$R^4$ is H or, in combination with $R^2$, >O;
provided that one of $R^1$ or $R^2$ and one of $R^3$ or $R^4$ must be H, and at least one of $R^1$, $R^2$, $R^3$, and $R^4$ must be other than H.

15. The compound of claim 14 where R is

$R^1$ and $R^3$ are HO—, and $R^2$ and $R^4$ are H.

16. The compound of claim 14 where R is

$R^1$ is $CH_3C_6H_4SO_2O-$, $R^3$ is

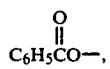

and $R^2$ and $R^4$ are H.

17. The compound of claim 14 where R is H and $R^2$ and $R^4$ are, in combination, >O.

18. The compound of claim 14 where R, $R^1$, $R^3$, and $R^4$ are H, and $R^2$ is —OH.

19. A compound of the formula

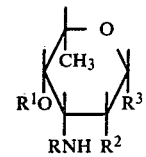

wherein
R and $R^1$, which may be the same or different, are

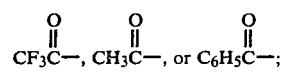

$R^2$ is

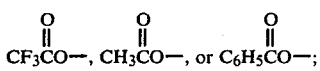

and
$R^3$ is

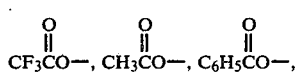

Cl—, or Br—.

20. The compound of claim 19 where R and $R^1$, are

and $R^2$ and $R^3$ are

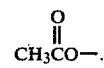

21. The compound of claim 19 where R and $R^1$ are

$R^2$ is

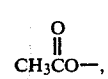

and $R^3$ is Br.

* * * * *